(12) United States Patent
Bayer et al.

(10) Patent No.: US 9,504,554 B2
(45) Date of Patent: Nov. 29, 2016

(54) MICROSTRUCTURED ABSORBABLE IMPLANT

(71) Applicant: BIOTRONIK AG, Buelach (CH)

(72) Inventors: Ullrich Bayer, Bad Doberan (DE);
Monika Badendieck, Rostock (DE);
Susanne Peters,
Admannshagen-Bargeshagen (DE);
Thomas Drobek, Rostock (DE);
Okechukwu Anopuo, Rostock (DE)

(73) Assignee: BIOTRONIK AG, Buelach (CH)

( * ) Notice: Subject to any disclaimer, the term of this patent is extended or adjusted under 35 U.S.C. 154(b) by 0 days.

(21) Appl. No.: 14/146,550

(22) Filed: Jan. 2, 2014

(65) Prior Publication Data

US 2014/0200652 A1    Jul. 17, 2014

Related U.S. Application Data

(60) Provisional application No. 61/752,992, filed on Jan. 16, 2013.

(51) Int. Cl.
| | |
|---|---|
| *C25F 3/04* | (2006.01) |
| *C25F 3/18* | (2006.01) |
| *A61F 2/06* | (2013.01) |
| *C22C 23/02* | (2006.01) |
| *C22C 23/04* | (2006.01) |
| *C25F 3/16* | (2006.01) |
| *A61L 31/02* | (2006.01) |
| *A61L 31/14* | (2006.01) |

(52) U.S. Cl.
CPC ............ *A61F 2/06* (2013.01); *A61L 31/022* (2013.01); *A61L 31/14* (2013.01); *A61L 31/148* (2013.01); *C22C 23/02* (2013.01); *C22C 23/04* (2013.01); *C25F 3/04* (2013.01); *C25F 3/16* (2013.01); *C25F 3/18* (2013.01); *A61L 2400/18* (2013.01)

(58) Field of Classification Search
USPC ......................................................... 205/677
See application file for complete search history.

(56) References Cited

U.S. PATENT DOCUMENTS

| | | | |
|---|---|---|---|
| 2009/0200178 A1* | 8/2009 | Piesslinger-Schweiger et al. ............................ | 205/680 |
| 2009/0324684 A1* | 12/2009 | Atanasoska et al. ......... | 424/426 |
| 2010/0076556 A1* | 3/2010 | Tomantschger ........ | A61L 17/10 623/11.11 |
| 2012/0143227 A1 | 6/2012 | Steckel et al. | |

FOREIGN PATENT DOCUMENTS

| | | |
|---|---|---|
| EP | 2668966 A1 | 12/2013 |
| WO | 2005/024099 A1 | 3/2005 |

OTHER PUBLICATIONS

EP14150896 European Search Report mailed Aug. 31 2016.

* cited by examiner

*Primary Examiner* — Nicholas A Smith
(74) *Attorney, Agent, or Firm* — Wagenknecht IP Law Group PC

(57) ABSTRACT

The production of microstructured surfaces in magnesium alloys, containing zinc as the major alloying element, in particular in absorbable implants such as stents, wherein microstructures in sizes of up to 5 μm (micrometers) are generated on a magnesium alloy base body of the absorbable implant, for example of the absorbable stent, by way of optionally combined, pickling and electrochemical micropolishing processes, and allow better adhesion of a polymer coating (including higher break resistance) and higher corrosion resistance. The microstructured surface is produced out of the bulk material and exhibits no delamination from the base material during the mechanical deformation of the implant.

16 Claims, 4 Drawing Sheets

MICROSTRUCTURED ABSORBABLE IMPLANT

CROSS REFERENCE TO RELATED APPLICATIONS

This application claims benefit of priority to U.S. patent application Ser. No. 61/752,992 filed Jan. 16, 2013; the contents of which are herein incorporated by reference in their entirety.

TECHNICAL FIELD

The invention relates to a microstructured surface made of a bioresorbable magnesium alloy, preferably containing zinc and/or aluminum as the main alloying element, and to a method for producing such microstructured surfaces, to the use of such microstructured surfaces in implants, to implants comprising such microstructured surfaces, and to a method for producing such implants. To this end, the invention can relate in particular to a stent as the implant.

BACKGROUND OF THE INVENTION

The implantation of stents has become established as one of the most effective therapeutic measures for the treatment of vascular diseases. Stents have the purpose of assuming a supporting function in hollow organs of a patient. For this purpose, stents featuring conventional designs have a filigree supporting structure comprising metal struts, which is initially present in compressed form for introduction into the body and is expanded at the site of the application. One of the main fields of application of such stents is to permanently or temporarily widen and hold open vascular constrictions, particularly constrictions (stenosis) of coronary vessels. In addition, aneurysm stents are known, which are used to stabilize damaged vessel walls.

Stents have a tubular base body, through which the blood continues to flow without impairment and the circumferential wall of which performs a supporting function for the vessel wall. The base body is frequently implemented as a mesh-like structure, having a plurality of individual strut sections that are connected to each other. The base body of the stent is made of an implant material. An implant material is a non-living material, which is used for applications in medicine and interacts with biological systems. A basic prerequisite for the use of a material as an implant material, which is in contact with the surrounding body area when used as intended, is the body friendliness thereof (biocompatibility). Biocompatibility shall be understood as the ability of a material to evoke an appropriate tissue response in a specific application. This includes an adaptation of the chemical, physical, biological, and morphological surface properties of an implant to the recipient's tissue with the aim of a clinically desired interaction. The biocompatibility of the implant material is also dependent on the temporal course of the response of the biosystem in which it is implanted. For example, irritations and inflammations can occur in a relatively short time, which can lead to tissue changes. Depending on the properties of the implant material, biological systems thus react in different ways. According to the response of the biosystem, the implant materials can be divided into bioactive, bioinert and degradable/resorbable materials.

Only metal implant materials for stents are of interest for the purpose of the present invention, and more particularly biocorrodible alloys of the element magnesium, containing zinc and/or aluminum as the main minor element. Such implants made of biocorrodible alloys can also be coated with biocompatible polymers.

As was already mentioned above, in addition to fulfilling the desired mechanical properties, a stent should be made of a biocompatible material so as to minimize rejection reactions. For example, stents are used in approximately 70% of all percutaneous interventions, however in a significant number of cases in-stent restenosis occurs due to excessive neointimal growth, which is caused by a strong proliferation of the arterial smooth muscle cells and a chronic inflammation reaction. A variety of approaches are employed to lower the restenosis rates.

One solution is the use of biocorrodible metal alloys, because in most instances a permanent supporting function by the stent is not required; the initially damaged vessel is able to regenerate. In DE 197 31 021 A1 it is thus proposed, for example, to fabricate medical implants from a metal material, the major constituent thereof being an element selected from the group consisting of alkali metals, alkaline earth metals, zinc and aluminum. Alloys based on magnesium and zinc are described as being particularly suited. Minor constituents of the alloys can be manganese, cobalt, nickel, chromium, copper, cadmium, lead, tin, thorium, zirconium, silver, gold, palladium, platinum, silicon, calcium, lithium, aluminum, and zinc. Furthermore, DE 102 53 634 A1 discloses the use of a biocorrodible magnesium alloy comprising contents of magnesium >90%, yttrium 3.7 to 5.5%, rare earth metals 1.5 to 4.4% and the remainder <1%, which is suited in particular for producing an endoprosthesis, for example in the form of a self-expanding or balloon-expandable stent.

Biocorrodible implants thus constitute a promising approach to reducing the restenosis rate. One problem with implementing such systems is the corrosion behavior of the implant. For example, fragment formation due to the corrosion process should be suppressed to the extent possible until the implant has grown into the vessel well. In addition, the supporting function should be preserved for the therapeutically specified time frame.

Magnesium alloys are gaining increasing technical importance as materials, in particular also in medical technology, for example as materials for implants. So as to provide a brief overview of the different magnesium alloys, the classification and designation of alloys and the effects of the most important alloying elements will be described in more detail at this point. The designation of magnesium alloys according to the ASTM standard has become widely accepted around the globe. The designations of alloys consist of two letters of the major alloying elements, followed by the rounded contents thereof in percent by weight. The ASTM code designations for the alloying elements of magnesium assign the following letters to these alloying elements: A for aluminum; B for bismuth; C for copper; D for cadmium; E for rare earths; F for iron; H for thorium; K for zirconium; L for lithium; M for manganese; N for nickel; P for lead; Q for silver; R for chrome; S for silicon; T for tin; W for yttrium; Y for antimony; and Z for zinc. The code may be followed by suffix letters that indicate various development stages of the corresponding alloys (A, B, C . . . ). These letters generally designate the content of impurities—with the letter X designating the alloy as an experimental alloy. Example: According to the code designation, the alloy AZ91 D is a magnesium alloy with a nominal content of 9% by weight of aluminum and 1% by weight of zinc in the fourth development stage.

Because of the very promising properties of magnesium as a material for medical technology, attempts have been ongoing for quite some time to positively influence the properties profile thereof using suitable alloying elements. The increase in the mechanical properties of magnesium by alloying additions is based on solid solution hardening, precipitation hardening or grain size hardening. In addition to the mechanical properties, alloying additions can also be used to influence other important properties such as the corrosion resistance, castability and weldability, among other things.

The effects of the most important alloying elements of magnesium are summarized below in alphabetical order.

Al: Aluminum is the "classic" alloying element for magnesium. Aluminum is added to increase the tensile strength and hardness. In addition to increasing strength, aluminum causes a marked improvement in the castability of magnesium. The drawback is the increased tendency toward microporosity.

Ag: In conjunction with the rare earth metals, silver dramatically increases the temperature stability and creep resistance, but causes an increased tendency toward corrosion.

Be: Beryllium is added to the magnesium melt in extremely low concentrations (<30 ppm) in order to reduce the oxidation tendency of the melt.

Ca: Calcium has an effective grain refining effect and increases the creep resistance. However, when processed by way of casting, an increased tendency to adhere to the mold and increased hot cracking susceptibility are to be expected.

Mn: The most important effect of adding manganese is the strong improvement in corrosion resistance (the iron content is controlled by lowering the solubility).

RE: All rare earth metals (the element yttrium shall be included here) form eutectic phase diagrams with magnesium with limited solubility on the Mg-rich side, which allows precipitation hardening. Because very stable precipitations form, these elements dramatically increase the temperature stability and creep resistance of the alloys.

Si: The addition of silicon worsens the castability. Because very stable silicides ($Mg_2Si$) can form, the creep resistance may be increased.

Zn: Like aluminum, zinc improves the castability and has a strength-increasing effect. However, as with aluminum, the tendency toward microporosity increases. Higher contents (>2%) increase the tendency toward hot cracking and worsen the weldability.

Zr: Zirconium is a very effective grain refining element. The fine grain size leads to an increase in the tensile strength, without lowering the strain. However, zirconium should not be added to melts containing aluminum or silicon because the reaction with these elements causes the grain-refining effect to be lost.

While magnesium alloys are used in many cases as cast alloys in lightweight construction (for example vehicle construction, aviation, mechanical engineering, consumer goods), what are known as wrought alloys are more customary in medical technology.

In non-ferrous metal metallurgy, wrought alloys refer to alloys that are distinguished from cast alloys by the ductility-favoring composition thereof, making them suitable for tasks such as rolling, pressing, drawing and forging, wherein the cast alloys are processed as liquid metal by pouring into a sand or permanent metal mold to form workpieces in the form of castings. Wrought alloys are an intermediate product, also referred to as a semi-finished product, the production of which is subject to some special characteristics as compared to cast alloys of the same type. In terms of the basic analytical composition, they differ only little from the cast alloys. Because the main requirement of a wrought alloy is the suitability for cold or hot forming, with the machinability optionally also being of importance, this may require that the content of some accompanying elements, which do not interfere with cast alloys, be limited and that elements that are suitable for promoting the further processing of the wrought alloy may need to be added.

The good properties of magnesium alloys are also offset by some negative aspects when using magnesium and the alloys thereof. Because magnesium crystallizes in the hexagonal close packing (hcp), the suitability for cold forming is poor in general. The reason for this is that below 225° C. deformation can only take place by two independent slip systems, and thus the condition for five independent slip systems (according to Von Mises) for a general change of shape is not met. Above approximately 225° C., the deformability increases almost suddenly because of the formation of new pyramidal slip planes—extensive deformations should thus occur above this temperature. Because of the hexagonal lattice structure and the tendency toward twinning, the magnesium material has thus become established as a wrought material only to a limited extent. The additional problem of the magnesium corroding requires the development of considerably more corrosion-resistant high-purity alloys with strict limits in terms of the contents of iron, nickel and copper (Fe<0.005%, Ni<0.001%, Cu<0.015%). For this reason as well, the available alloying range of magnesium as a wrought material is even further limited than for the cast alloys. Mg—Al alloys, such as AZ31, AZ61 and AZ80, play also a considerable role here, for example in lightweight construction. In addition, alloys containing zinc as the main alloying element, such as ZK60, exist. These alloys are processed by way of hot forming such as rolling, extrusion and forging at temperatures above 350° C. During a downstream cold forming operation, only small degrees of deformation are tolerated, otherwise cracks will form in the material. In the recent past, the development of wrought alloys of magnesium has been the focus of intensified interest again, because magnesium alloys are also to be used increasingly in medical technology workpieces, for example as implants, and more particularly as stent base bodies.

The prior art, for example DE 2008 10040143, describes magnesium alloys that contain yttrium and additional rare earth metals, because such an alloy stands out due to the physicochemical properties thereof and the high biocompatibility, in particular of the decomposition products thereof. Particularly preferred are magnesium alloys of the WE series, notably WE43, and magnesium alloys having a composition of 5.5 to 9.9% by weight of rare earth metals, of which yttrium can account for 0.9 to 5.5% by weight and the remainder ≤1% by weight, wherein the remainder can contain zirconium and/or silicon, and wherein magnesium accounts for the content in the alloy which is missing to make up 100% by weight. These magnesium alloys have already confirmed their particular suitability in experiments and initial clinical tests, which is to say they exhibit high biocompatibility, favorable processing properties, good mechanical characteristics and corrosion behavior that is adequate for the application purposes. In the present case, the collective term "rare earth metals" shall include scandium (21), yttrium (39), lanthanum (57) and the 14 elements following lanthanum (57), which is to say cerium (58), neodymium (60), promethium (61), samarium (62), europium (63), gadolinium (64), terbium (65), dysprosium (66), holmium (67), erbium (68), thulium (69), ytterbium (70) and lutetium (71).

Magnesium alloys for absorbable stents are often times provided with one or more coatings, for example a polymeric and/or optionally also active agent-containing coating, and the magnesium alloys must therefore have surface morphologies that exhibit sufficient adhesive action with respect to the coating, for example a polymeric primary coating (base coat). Otherwise the coating, and the polymer in particular, will tear open during dilation of the stent in the areas of the stents that have been deformed the most (for example on the insides of the arcs) and the metal will be exposed. The results are increased corrosion and a reduced supporting effect of the stent. This problem is not as pronounced in the WE 43 type magnesium alloys that have been used until now. The reason for this lies in the precipitations that are present due to the alloy, which in addition to the raised grain boundaries lead to a certain degree of surface roughness, even in electropolished surfaces. This in turn causes satisfactory adhesion of subsequent polymeric finishing coats.

Different novel and advantageous magnesium alloys, containing zinc as the essential major alloying element, for example magnesium alloys such as Z50 (95% by weight Mg; 5% by weight Zn) exhibit no tendency toward the formation of secondary phases and thus tend less toward precipitations due to the alloy. In addition, the grain boundaries thereof are not raised after electropolishing. In these magnesium alloys, containing zinc as the essential main alloying element, a considerable effect, which favors the polymer adhesion, is thus eliminated because of the very smooth surfaces following electropolishing.

Several experiments that improve the surface properties of implants, and of stents in particular, are already known from the prior art. US 2010/0305684, for example, discloses a Mg stent, which is coated with a ceramic layer so as to increase the corrosion resistance. By way of electrochemical fluorination, the Mg base body is provided with an intermediate $MgF_2$ layer, which similarly to the final ceramic layer is intended to delay the corrosion of the Mg base body by preventing fractures and cracking. However, US 2010/0305684 does not contain any suggestions with regard to the surface characteristics of the intermediate $MgF_2$ layer that is generated by way of electrochemical fluorination.

In addition, US 2006/0198869 discloses, in very general terms, the production of biodegradable stents. During the production, an etching step is carried out, and a coating made of polymer is also disclosed. The document also describes the creation of microstructures measuring 15 to 250 micrometers (m) in size by way of micro-etching. However, these microstructures according to US 2006/0198869 are formed only on the structural element that is additionally applied to the surface, in particular by and/or in the polymer material. In contrast, microstructuring of the surface of the Mg base body within the surface of the Mg alloy and/or the surface of the Mg alloy itself does not take place in US 2006/0198869.

The aim is thus to structure the surfaces of magnesium alloys, preferably containing zinc and/or aluminum, in particular containing zinc, as the essential main alloying element, in such a way that a roughness is achieved even in these magnesium alloys, which allows optimal adhesion of coatings, which is to say, for example, optimal polymer adhesion and/or optimal adhesion of an active agent-containing base coat in the case of a polymeric and/or optionally active agent-containing base coat.

The object according to the invention is thus in particular to structure the surfaces of such magnesium alloys, preferably containing zinc and/or aluminum, in particular zinc, as the essential main alloying element, for example magnesium alloys such as Z50, so that these surfaces exhibit increased adhesive strength for polymeric finishing coats and exhibit no drawbacks in terms of the breakage behavior. Another object is that of increasing the corrosion resistance of the base material, which is to say of the magnesium alloys, preferably containing zinc and/or aluminum, in particular zinc, as the essential main alloying element.

SUMMARY OF THE INVENTION

The present object is achieved by the subject matter of the independent claims. In order to achieve the object, the invention proposes in particular a surface that is microstructured in a novel way and made of a bioresorbable magnesium alloy, preferably containing zinc and/or aluminum as the essential main alloying element, and a method for producing such microstructured surfaces, the use of such microstructured surfaces in implants, implants comprising such microstructured surfaces, and a method for producing such implants. To this end, according to the invention the implant is in particular a stent, comprising such microstructured surfaces, including the production thereof. Preferred embodiments of the subject matter according to the invention will be described in the following detailed description and can be combined with each other, to the extent the person skilled in the art considers this to be expedient.

In summary, the basic concept of the present invention relates to the production of microstructured surfaces of magnesium alloys, preferably containing zinc and/or aluminum, in particular zinc, as the main alloying element, especially in absorbable implants such as stents, for example, wherein microstructures having a (grain) size of up to 10 μm (micrometers), in particular up to 7 μm (micrometers), and preferably up to 5 μm (micrometers), on a magnesium alloy base body of an absorbable implants, for example of an absorbable stent, which are modified by way of etching (pickling) and electrochemical micropolishing, and preferably by the combining etching (pickling) and electrochemical micropolishing, allow better adhesion of a polymer coating, greater resistance to tearing under mechanical stress (referred to as break resistance) and higher corrosion resistance. For example, an absorbable implant, for example a stent, made of a very fine-grained magnesium base alloy, which is to say a magnesium base alloy that is provided with a protruding (grain) size in the micrometer range, is given a microstructured surface by way of a specific surface treatment method. This microstructured surface according to the invention is characterized both by high adhesive strength for polymer layers and by an increased corrosion resistance. The microstructured surface is produced out of the bulk material and exhibits no delamination from the base material during the mechanical deformation of the implant.

The present invention thus overcomes a number of problems and drawbacks of the prior art, such as in particular the following: insufficient adhesive action with respect to polymer layers (which is to say to the outside); insufficient adhesion of the surfaces to the bulk material (which is to say to the inside); the negative impact on the mechanical properties of the implant or stent during dilatation (notch effects and the resulting small dilatation diameter during the first and second fractures); and the absent or insufficient corrosion protection action. The invention thus achieves both the object of improving the polymer adhesion to absorbable implants, in particular to absorbable magnesium stents (AMS), and the object of increasing the corrosion resistance of such implants or stents. It improves essential properties of the base body of the magnesium alloy for the application of such absorbable implants, particularly stents. Because of the biodegradation property and the good biocompatibility of magnesium alloys, they have attained great interest as materials used for implants, and for stents in particular, and in a surprising and advantageous manner the present invention is able to overcome some of the drawbacks that still exist in the prior art for these alloys. For example, in addition to magnesium (Mg) and calcium (Ca), zinc (Zn), which is preferred as an alloying addition, is an important trace element for the body. Contrary to Y and the rare earths, for example, Zn, when used as an alloying addition, is not the subject of controversial discussions with regard to the damaging interactions of resorbable implants.

The microstructured surfaces according to the invention of magnesium alloys, containing zinc and/or aluminum, in particular zinc, as the main alloying element, in particular in absorbable implants such as stents, can be analyzed and verified by techniques that are known per se to the person skilled in the art for chemical, metallurgical and/or structural analysis.

Within the scope of the present invention, a magnesium alloy shall always be understood to mean an alloy containing magnesium as the major constituent. Being the major constituent, magnesium is thus the element that represents the largest percentage by weight in the alloy. Main alloying elements encompasses those elements that, after magnesium, account for the largest percentages by weight in the alloy.

DETAILED DESCRIPTION OF THE INVENTION

Figure 1:
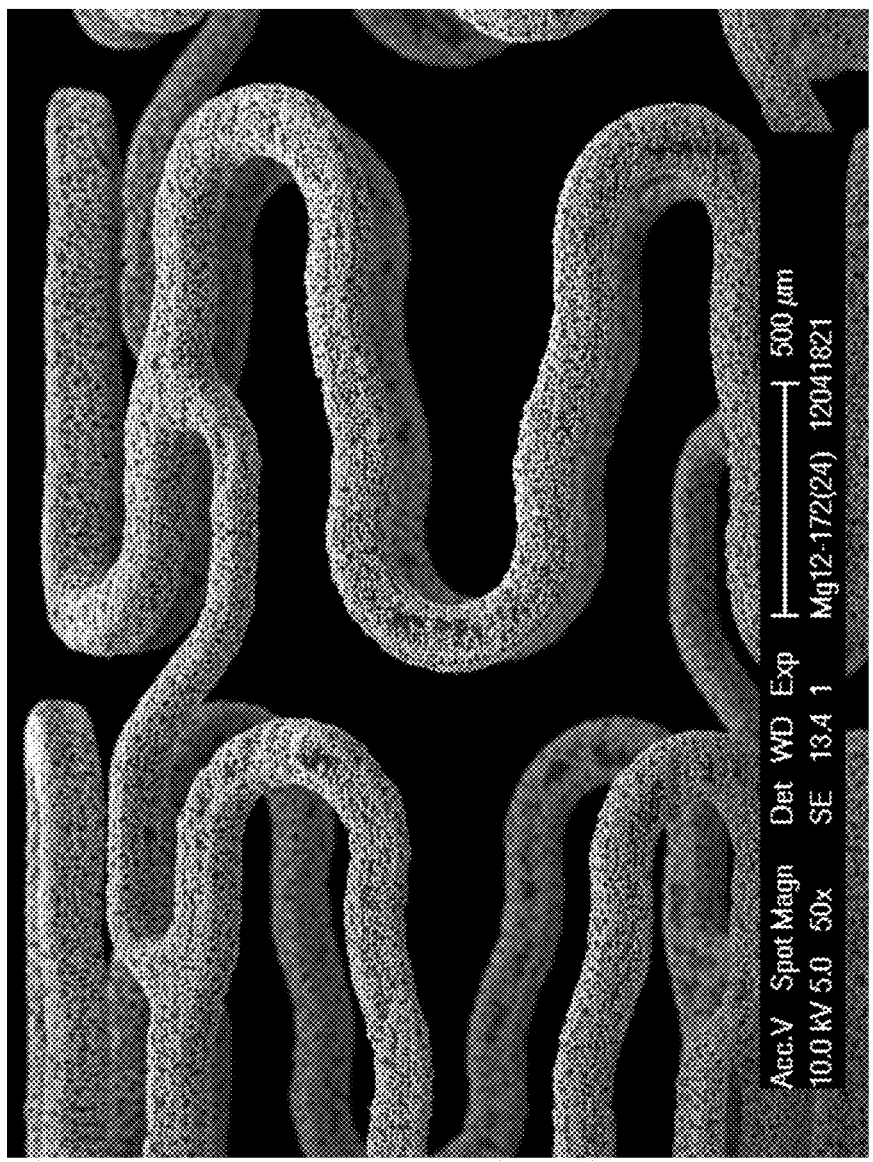
FIG. 1: shows the microstructured stent surface according to exemplary embodiment 1 (scanning electron microscopy).

The invention thus relates to a method for producing a microstructured surface from a bioresorbable magnesium alloy, preferably containing zinc and/or aluminum, characterized in that a surface of a bioresorbable magnesium alloy is treated with a pickling process and an electropolishing process, preferably by a combined pickling and electropolishing process, wherein
  a) the surface to be treated comprises or consists of a grain structure having a mean grain size of ≤10 μm, preferably of ≤7 μm, and still more preferably of ≤5 μm, a bioresorbable magnesium alloy, containing magnesium as the major constituent and zinc and/or aluminum as the main alloying elements, preferably containing zinc as the main alloying element; and wherein
  b) the magnesium alloy comprises or consists of a composition containing
    magnesium in a quantity of 78.0 to 98.99% by weight, preferably 88.5 to 96.9% by weight, still more preferably 91.8 to 95.8% by weight, and most preferably 94.0 to 95.4% by weight; and
    preferably zinc and/or aluminum, preferably zinc, in a total quantity of 1 to 20% by weight, preferably 3 to 10% by weight, still more preferably 4 to 7% by weight and most preferably 4.5 to 5.5% by weight; and
    optionally one or more additional alloying additions that are customary for and physiologically compatible with magnesium alloys, in particular calcium in a total quantity of 0.01 to 2% by weight, preferably 0.1 to 1.5% by weight, still more preferably 0.2 to 1.2% by weight, and most preferably 0.1 to 0.5% by weight; in each case, based on the total magnesium alloy of 100% by weight.

The invention preferably relates to the above-described method for producing a microstructured surface from a bioresorbable magnesium alloy, containing zinc and/or aluminum, in which a surface of a bioresorbable magnesium alloy is treated with a pickling process and an electropolishing process, preferably by a combined pickling and electropolishing process, characterized in that the magnesium alloy comprises or consists of a composition containing
  magnesium in a quantity of 80 to 99% by weight, preferably 90 to 97% by weight, still more preferably 93 to 96% by weight, and most preferably 94.5 to 95.5% by weight; and
  zinc and/or aluminum, preferably zinc, in a quantity of 1 to 20% by weight, preferably 3 to 10% by weight, still more preferably 4 to 7% by weight, and most preferably 4.5 to 5.5% by weight;
  and optionally one or more alloying additions that are customary for and physiologically compatible with magnesium alloys, in particular calcium in a total quantity of 0.01 to 2% by weight, preferably 0.1 to 1.5% by weight, still more preferably 0.2 to 1.2% by weight, and most preferably 0.1 to 0.5% by weight;
in each case, based on the total magnesium alloy of 100% by weight.

According to the invention, the surface of a magnesium alloy base body, for example of an absorbable implant, and more particularly of an absorbable stent, for example, is thus modified by way of etching (optionally also referred to as "pickling" or "pickling process") and electrochemical micropolishing. Both etching (pickling) and electropolishing are common methods for a person skilled in the art, which are also known and widely employed in medical technology.

Etching or a pickling process within the meaning of the present invention shall be understood to mean a method that generally takes place in acids or in acid-containing mixtures and causes the intensive cleaning and activation of metal surfaces, usually accompanied by minor material removal. This results in metallically pure surfaces, which are free from oxides and contamination by foreign metals. Etching or pickling preferably affects the areas of a metal structure, which compared to the adjoining area have a lower corrosion resistance to the respective etching or pickling solution. These can be grains, for example, which have a slightly modified alloy composition compared to the respective neighboring grain. Preferably the grains that are chemically attacked are those, in which the alloying elements that increase the corrosion resistance of the alloy are present in a lower concentration than in the remaining grains. Etching or pickling can be carried out both chemically and electrolytically (anodically). Etching or pickling agents generally contain mineral acids and an oxidizing agent, as well as additives to improve the etching or pickling result and to reduce harmful substances.

An electropolishing process (electropolishing) is considered an electrochemical method for generating and optimizing a variety of technical-functional and/or decorative properties and for achieving freedom from burrs and/or freedom from particles of surfaces by the treatment in an electrolyte while applying a voltage. Electropolishing methods are industrially proven and are known to a person skilled in the art as reliable and economical for a variety of applications, in particular wherever increased demands exist with regard to the function and appearance of metallic surfaces. Electropolishing acts in the micro-range, without modifying shapes and macro-structures, removing a thin material layer from the material surface, without mechanical or thermal stress of the treated material, by way of anodic dissolution. All impurities, particles, microcracks, structural defects and local tensions contained therein are thereby eliminated. The increased removal of corners and edges caused by flux line densification effects causes the reliable deburring and smoothing thereof. Electropolished surfaces are free from burrs and particles, metallically pure, shiny, smooth in the micro-range and closed, and have the optimal properties of the base material.

The term "combined" within the meaning of the present invention for the etching and electropolishing process does not mean that both processes have to be carried out at the same time. However, the latter is preferred. The etching process ("etching", also referred to as "pickling" or "pickling process") and electrochemical micropolishing can be carried out as separate methods, for example when an already (pre-)etched magnesium alloy base body is to be machined or finished not until later, or an already electropolished magnesium alloy base body is to be machined or finished again by way of electropolishing, and can, on the other hand, also preferably be carried out by simultaneously combining the etching and electrochemical micropolishing. If the etching and electropolishing process is preferably combined at the same time, the transition from etching to electropolishing is characterized by applying the voltage for the electropolishing process.

According to the invention, the (grain) size of the microstructures in the micrometer range of up to 10 μm (micrometers), in particular up to 7 μm (micrometers), and preferably up to 5 μm (micrometers), is of importance, in particular it is stated as a statistic average. The grain sizes of particularly preferred magnesium alloys according to the invention, for example, have a statistic average of 1 to 5 μm, which is to say that 95% of all measured grains are present in this size range. The mean grain size is determined according to the method described in DIN EN ISO 643:2003. For determining the grain size, standardized image series charts from ASTM E 112 are used (the point of contact for comparison images is ASTM, 100 Barr Harbor Drive, Philadelphia, Pa. 19428-3914, USA; reference number ADJ 12-501120-10).

The term "microstructure" within the scope of the present invention shall be understood to mean a three-dimensional surface landscape or surface structure in the micrometer range, which is formed by a grain structure that has a (grain) size up to 10 μm, in particular up to 7 μm, and preferably up to 5 μm, and that is formed after dissolving individual grains out of the surface (for example by way of pickling and electropolishing). This three-dimensional surface landscape or surface structure, which is to say the three-dimensional grain structure of the above size that is present on the surface, has depressions (craters) on the surface which have a maximum depth of approximately 3 μm protruding into the surface (crater depth) and a maximum lateral diameter of up to 10 μm (crater width). This three-dimensional surface landscape or surface structure is thus a crater structure having a maximum crater depth of 3 μm and a maximum crater width of 10 μm. The invention thus also relates to a method for producing a microstructured surface, characterized in that the generated microstructured surface has a microstructure made of a grain structure having raised grain boundaries and neighboring depressions, preferably a microstructure made of a grain structure having raised grain boundaries and neighboring depressions designed as crater-shaped microstructures. Preferred methods according to the invention for producing a microstructured surface are also characterized in that a microstructured surface having a microstructure made of a grain structure is generated, which corresponds to a mean grain size of 1 to 8 μm, preferably of 2 to 7 μm, still more preferably of 3 to 6 μm, and most preferably of 3 to 5 μm.

Within the meaning of the present invention, the term "degradable magnesium stent" shall mean that the base body of the magnesium stent degrades in a physiological environment, in particular in the vascular system of a human or animal body, which is to say it is decomposed so that the stent loses its integrity. According to the invention, the magnesium stent does not degrade until the function of the stent is no longer physiologically useful or necessary, which is to say when the traumatized tissue of the vessel has healed and the stent no longer has to remain in the vessel lumen.

According to the present invention, the degradable magnesium stent or magnesium stent body comprises or consists of a biocorrodible magnesium alloy. A magnesium alloy in the present case shall be understood as a metal structure, the major constituent of the alloy being magnesium. The major constituent is the alloying component with the highest percentage by weight in the alloy. In addition to magnesium as the major alloying component, the alloys according to the present invention preferably contain zinc and/or aluminum as minor alloying components. Magnesium alloys containing zinc as the main secondary alloying constituent are particularly preferred for this purpose.

Within the scope of the invention, the composition of the magnesium alloy, comprising magnesium as the major constituent and zinc and/or aluminum, preferably zinc, as the main alloying element, is to be selected such that it is biocorrodible. In this description, "biocorrodible" and "bioabsorbable" are used analogously to each other.

According to the invention, the metal base body of the implant or of the stent is made of a biocorrodible magnesium alloy, preferably containing zinc and/or aluminum, preferably zinc, as a further alloying constituent. Biocorrodible as defined by the invention denotes alloys, which undergo degradation or reorganization in a physiological environment, so that the part of an implant, in particular of a stent, that is made of the alloy is no longer present, either entirely or at least predominantly. The composition of the alloy is thus to be selected such that it is biocorrodible. A possible test medium for testing the corrosion behavior of a potential alloy is synthetic plasma, as that which is required according to EN ISO 10993-15:2000 for biocorrosion analyses (composition NaCl 6.8 g/l, $CaCl_2$ 0.2 g/l, KCl 0.4 g/l, $MgSO_4$ 0.1 g/l, $NaHCO_3$ 2.2 g/l, $Na_2HPO_4$ 0.126 g/l, $NaH_2PO_4$ 0.026 g/l). For this purpose, a sample of the alloy to be analyzed is stored in a closed sample container with a defined quantity of the test medium at 37° C. The samples are removed at intervals—which are matched to the anticipated corrosion behavior—ranging from a few hours to several months and analyzed for traces of corrosion in the known manner. The synthetic plasma according to EN ISO 10993-15:2000 corresponds to a blood-like medium and thus is a possible option to reproducibly simulate a physiological environment as defined by the invention.

According to the invention, the base body is made of a biocorrodible magnesium alloy. In addition to magnesium and zinc and/or aluminum, the biocorrodible magnesium alloy preferably contains alloying additions that are customary for magnesium alloys. One or more metals from the group consisting of manganese (Mn), silver (Ag), cerium (Ce), silicon (Si), zirconium (Zr), lithium (Li) and calcium (Ca) are possible further alloying elements. With Mg alloys containing zinc as the major alloying element, it is also possible to include aluminum (Al) in the above group of further alloying elements, and with Mg alloys containing aluminum as the major alloying element, it is possible to include zinc (Zn). These further alloying additions are most preferably calcium (Ca) and/or zirconium (Zr), because such alloys stand out with their physicochemical properties and high biocompatibility, in particular also of the decomposition products thereof.

Rare earth metals are rather of subordinate significance as further alloying additions for the present invention, and alloys having higher contents of rare earth metals may possibly be even unsuited. In the present case, the collective term "rare earth metals" shall include scandium (21), yttrium (39), lanthanum (57) and the 14 elements following lanthanum (57), which is to say cerium (58), praseodymium (59), neodymium (60), promethium (61), samarium (62), europium (63), gadolinium (64), terbium (65), dysprosium (66), holmium (67), erbium (68), thulium (69), ytterbium (70) and lutetium (71).

Within the scope of the invention, such rare earth metals or the further additional alloying elements can, as will be described hereafter, be present in certain quantities in the magnesium alloys containing zinc and/or aluminum, preferably zinc, as the essential major alloying element, wherein the information is based on the percent by weight in the alloy, and magnesium and zinc and/or aluminum account for the remaining content in the alloy that is missing to make up 100% by weight. A person skilled in the art will know that this quantity information can vary slightly because of production-related impurities and will be in a position to correctly classify these potential slight deviations, for example in the assessment whether a composition falls within a defined range.

Within the scope of the invention, the total quantity of rare earth metals in the alloys should preferably be no more than 3% by weight, preferably no more than 2% by weight, and most preferably no more than 1% by weight, in each case based on the total alloy of 100% by weight. The quantity of rare earth metals can thus range between 1 and 3% by weight, preferably between 1 and 2% by weight, and most preferably between 0 and 1% by weight, wherein magnesium and zinc and/or aluminum together make up the content in the alloy that is missing to make up 100% by weight.

Within the scope of the invention, the quantity of alloying elements selected from the group consisting of zinc (Zn), aluminum (Al), manganese (Mn), silver (Ag), cerium (Ce), silicon (Si), zirconium (Zr), calcium (Ca) and lithium (Li), preferably from the group consisting of zinc (Zn), aluminum (Al), calcium (Ca) and zirconium (Zr) in the alloys, should be no more than 11% by weight, preferably no more than 8% by weight, and most preferably no more than 7% by weight, in each case based on the total alloy of 100% by weight. The total quantity of these additional alloying elements can thus range between 0 and 11% by weight, preferably between 0 and 8% by weight, and most preferably between 0 and 7% by weight, wherein magnesium accounts for the content in the alloy that is missing to make up 100% by weight.

In an exemplary embodiment of the invention, the magnesium alloy has a composition made of 94.75% by weight magnesium, 5% by weight zinc and 0.25% by weight calcium. In a further exemplary embodiment of the invention, the magnesium alloy has a composition made of 95% by weight magnesium and 5% by weight zinc.

Magnesium alloys that contain zinc in a quantity of up to 11% by weight, in particular zinc in a quantity of 2 to 10% by weight, are also preferred. Most preferred are magnesium alloys that, in addition to the magnesium and zinc in the quantities described above, also contain further customary alloying additions in the composition, which in sum account for ≤2% by weight of the total alloy. Examples include compositions that contain calcium in a quantity of 0.05 to 1% by weight and/or yttrium in a quantity of 0.5 to 1% by weight and/or manganese in a quantity of 0 to 0.5% by weight and/or silver in a quantity of 0 to 1% by weight and/or cerium in a quantity of 0 to 1% by weight and/or zirconium in a quantity of 0 to 1% by weight and/or silicon in a quantity of 0 to 0.4% by weight and/or lithium in a quantity of 0 to 1% by weight, wherein the information is based on the weight percent of the total alloy, and magnesium as well as production-related impurities account for the remaining content in the alloy that is missing to make up 100% by weight.

In principle, stents have a supporting structure, which is suited to appropriately support the wall of a vessel so as to be able to expand the vessel or bridge an aneurysm. For this purpose, stents are introduced into the vessel in a compressed state and then expanded at the site to be treated and pressed against the vessel wall. This expansion can take place, for example, by way of a balloon catheter. As an alternative, self-expanding stents are also known. These are composed of a superelastic metal, such as nitinol, for example. Such stents can be provided with a surface that is microstructured in accordance with the invention.

Stents are presently divided into two basic types, which are permanent stents and degradable stents. Permanent stents are designed to remain in the vessel for an indefinite period. In contrast, degradable stents are decomposed in a vessel over a predetermined time period. Degradable stents preferably do not decompose until the traumatized tissue of the vessel has healed, and hence the stent no longer needs to remain in the vessel lumen. Known degradable stent materials include, for example, degradable metal alloys, polymers or composite materials, which exhibit sufficient structural load-bearing capacity to be able to support the vessel lumen over a predetermined time period.

Within the meaning of the present invention, all customary stent geometries can be used as degradable magnesium stents according to the invention. Stent geometries as described in U.S. Pat. No. 6,896,695, US 2006/241742, U.S. Pat. No. 5,968,083 (Tenax), EP 1 430 854 (helix design), U.S. Pat. No. 6,197,047 and EP 0 884 985 are particularly preferred.

The magnesium stent according to the invention can preferably be provided with a coating, optionally also as an additional top coat, comprising or consisting of one or more biodegradable polymers and/or the blends thereof, such as PLLA, PLGA and PCL.

The object of the invention is thus also achieved by providing a microstructured surface that is made of a bioresorbable magnesium alloy, preferably containing zinc and/or aluminum, preferably zinc, as the major alloying element, wherein the surface that is microstructured according to the invention is characterized in that
  a) the surface comprises or consists of a grain structure having a mean grain size of ≤10 μm, preferably of ≤7 μm, and still more preferably of ≤5 μm, of a bioresorbable magnesium alloy, containing magnesium as the major constituent and zinc and/or aluminum as the major alloying elements, preferably containing zinc as the major alloying element; and wherein
  b) the magnesium alloy comprises or consists of a composition containing
    magnesium in a quantity of 78.0 to 98.99% by weight, preferably 88.5 to 96.9% by weight, still more preferably 91.8 to 95.8% by weight, and most preferably 94.0 to 95.4% by weight; and
    preferably zinc and/or aluminum, preferably zinc, in a total quantity of 1 to 20% by weight, preferably 3 to 10% by weight, still more preferably 4 to 7% by weight and most preferably 4.5 to 5.5% by weight; and
    optionally one or more further alloying additions that are customary for and physiologically compatible with magnesium alloys, in a total quantity of 0.01 to 2% by weight, preferably 0.1 to 1.5% by weight, still more preferably 0.2 to 1.2% by weight, and most preferably 0.1 to 0.5% by weight;
  in each case based on the total magnesium alloy of 100% by weight,
wherein the microstructured surface preferably comprises or consists of a microstructure having raised grain boundaries and neighboring depressions, preferably a microstructure made of raised grain boundaries and neighboring depressions designed as crater-shaped microstructures.

The invention comprises in particular a microstructured surface, in which the magnesium alloy comprises or consists of a composition containing
  magnesium in a quantity of 80 to 99% by weight, preferably 90 to 97% by weight, still more preferably 93 to 96% by weight, and most preferably 94.5 to 95.5% by weight;
  zinc and/or aluminum, preferably zinc, in a quantity of 1 to 20% by weight, preferably 3 to 10% by weight, still more preferably 4 to 7% by weight, and most preferably 4.5 to 5.5% by weight; and
  optionally one or more further alloying additions that are customary for and physiologically compatible with magnesium alloys in a total quantity of 0.01 to 2% by weight, preferably 0.1 to 1.5% by weight, still more preferably 0.2 to 1.2% by weight, and most preferably 0.1 to 0.5% by weight;
in each case based on the total magnesium alloy as 100% by weight.

Further preferred microstructured surfaces are characterized in that the microstructured surface comprises or consists of a microstructure made of a grain structure that corresponds to a grain size of 1 to 8 μm, preferably of 2 to 7 μm, still more preferably of 3 to 6 μm, and most preferably of 3 to 5 μm.

The object of the invention is further achieved by using a microstructured surface and by providing an implant. The invention thus also relates to implants comprising a microstructured surface according to the invention as described above that is made of a bioresorbable magnesium alloy, preferably containing zinc and/or aluminum, preferably zinc, as the major alloying element. Such implants according to the invention, comprising a microstructured surface according to the invention as described above that is made of the bioresorbable magnesium alloy, preferably containing zinc and/or aluminum, preferably zinc, as the major alloying element, can be provided with a coating that is made of one or more biocompatible polymers, preferably one or more bioresorbable polymers. Such an implant according to the invention is in particular a stent.

Further details with regard to achieving the object according to the invention or the present invention will be described hereafter.

The invention is based on the combined realization that both a smaller average grain size in a structure of a magnesium alloy and grains having a below-average content of the minor alloying constituents zinc and/or aluminum in the fine-grained structure of the magnesium alloy result in an increased corrosion rate in these regions. The so-called grain refining is created in that a smaller, finer grain is formed in the structure of the magnesium alloy, for example, due to heat treatment during production, such as during extrusion, of a material made of magnesium alloy. At the same time, regions containing grain and/or fine grain can be formed in the structure of the magnesium alloy, in which the grains have a below-average content of the minor alloying constituents zinc and/or aluminum, and additionally regions containing grain and/or fine grain can be formed in the structure of the magnesium alloy, in which the grains have a slightly higher zinc and/or aluminum content than the mean (average) zinc or aluminum alloy content. In a material that is made of a magnesium alloy, containing zinc and/or aluminum as the minor alloying constituents, thus regions having differing average grain sizes and/or differing local (grain-based) zinc and/or aluminum contents, and thus having differing corrosion properties, can be formed.

According to the invention, these differences in the corrosion behavior of regions of a material that is based on magnesium alloy, containing zinc and/or aluminum as the major alloying element, depending on the grain size and/or the local (grain-based) zinc and/or aluminum contents, are utilized so as to attain, through targeted corrosion, an overall microstructured surface that is made of a biocorrodible magnesium alloy, containing zinc and/or aluminum as the major alloying elements, and has increased corrosion resistance, and thereby influence in particular also the corrosion behavior, the degradation process and the degradation time of an implant, preferably of a stent, comprising such a microstructured surface, in an advantageous manner or in advance in a calculable manner; according to the invention, the corrosion behavior is also utilized to improve the adhesive action for polymer coatings that are to be applied.

The time period for the degradation begins immediately after implantation and ends at a predeterminable time, which satisfies the therapeutic specifications and requirements in regard to safety. This time period preferably extends over 2 to 6 weeks immediately after implantation. For example, a stent has generally grown into the vessel wall during this time period and the wall has sufficiently regenerated, so that a further supporting function is no longer required.

Grain sizes and grain compositions that are particularly suited for the invention comprise magnesium alloys containing zinc and/or aluminum as the major alloying elements, which are wrought alloys. The invention thus also relates to a method for producing a microstructured surface, in which the magnesium alloy that is used is a wrought alloy and/or has a heterogeneous and/or no preferred crystallographic orientation. In non-ferrous metal metallurgy, wrought alloys refer to alloys that are distinguished from cast alloys by a composition favoring the ductility thereof, making them suitable for tasks during rolling, pressing, drawing, or forging. The wrought alloys within the meaning of the present invention shall also be understood as such ductile compositions.

The term corrosion in the present example refers to the reaction of the metallic material with the environment thereof; wherein a measurable change of the material is caused, which—when using the material in a component—results in an impairment of the function of the component. A corrosion system is composed of the corroding metal material and a (liquid) corrosion medium, which in the composition thereof simulates the conditions in a physiological environment, or is a physiological medium, particularly blood. With respect to the material, corrosion is influenced by factors such as the composition and pretreatment of the alloy, microscopic and sub-microscopic inhomogeneities, peripheral zone properties, temperature and stress states, and in particular the composition of a layer covering the surface. With respect to the medium, the corrosion process is influenced by the conductivity, temperature, temperature gradients, acidity, surface area to volume ratio, concentration difference, and flow rate.

In a further concept, the invention relates to a method for producing a stent according to the invention, comprising the following steps: a) providing a stent or a stent precursor product as an extruded sleeve having an outside diameter of 2.00 mm and a wall thickness of 190 µm; b) treating the stent or a stent precursor product by laser cutting the extruded sleeve to form a laser-cut stent structure;

c) reaming the laser-cut stent structure so as to remove slag adhering to the laser cutting edges; and d) etching (pickling) and electropolishing according to the invention.

This method employs stents or stent precursor products having a structure made of a biocorrodible magnesium alloy.

Absorbable stents made of magnesium alloys, such as Z50 for example (95% by weight Mg; 5% by weight Zn) and others, are preferably produced by means of an extrusion process within the scope of the invention. Through the specific extrusion process, for example, a very fine-grained structure in the micrometer range, as stated above, of ≤10 µm, ≤7 µm or ≤5 µm is formed, and in particular with a mean grain size of 1 to 5 µm, and preferably 2 to 4 µm, in the magnesium alloy. The sleeve-shaped semi-finished product thus produced is then cut by means of laser cutting to form a stent-shaped structure. Thereafter, according to the invention a preferably combined pickling and electropolishing process is carried out, which results in a microstructured surface of the magnesium alloy. The pickling rate is such that neighboring grains are removed to varying degrees. This effect is based on differing crystallographic orientations of the grains in the structure of the magnesium alloy and on the differences thereof in the contents of dissolved Zn and/or Al.

The invention thus also relates to a method for producing a microstructured surface, in which the surface to be treated comprises or consists of a magnesium alloy made of a grain structure, in which different grains having differing zinc contents and/or aluminum contents are present. In this method for producing a microstructured surface, the surface of the magnesium alloy to be treated is characterized in particular by a grain structure having to a mean grain size of 1 to 10 µm, preferably of 1 to 7 µm, still more preferably of 1 to 5 µm, and most preferably of 2 to 4 µm.

The selective etching step described above achieves two fundamental effects:

First, the resulting surface has microstructure widths that correspond, for example, to those having a mean grain size of 1 to 5 µm, and in particular of 2 to 4 µm. This means that crystallographically favorably oriented grains of the magnesium alloy having a slightly higher Zn or Al content than the mean Zn or Al alloy content are not corroded (or are corroded less), however some or all of the neighboring grains are removed by pickling. Structures are thus created, at least in the surface of the magnesium alloy or of the implant or stent, which preferably have a crater-shaped cross-section and which exhibit high cohesive forces with respect to the bulk material located beneath (inside) and an extremely high adhesive action with respect to the polymer layers applied subsequently (outside) to the surface of the magnesium alloy or the implant or stent.

Secondly, the chemical removal of less resistant surface regions by means of pickling and electropolishing increases the integral corrosion resistance of the surface of the magnesium alloy or of the implant or stent. This results in a longer useful life of the surface of the magnesium alloy or of the implant or stent under physiological conditions, and more particularly independently of whether or not a polymeric coating is applied.

Surprisingly, it has been found that the inventive combination of an alloy composition having the grain size of the bulk material indicated above and in the examples, in particular with a lacking preferred crystallographic orientation of the grains in the alloy composition due to the extrusion process (for example impact extrusion) and subsequent recrystallization annealing, with the surface treatment method reliably and reproducibly leads to the microstructured surfaces according to the invention with the described advantages.

Polishing is an important surface structuring method. The result it should produce is atomistically flat surfaces with negligible substrate effects. However, due to differing reactivities of the grains, a highly grain-dependent metal removal takes place. Some grains are higher than others after polishing, wherein the resulting differences in height between the crystallites are dependent on: the polishing process, polishing duration, and combination of the orientations of neighboring grains as well as the composition of the individual grains.

The following model analysis describes the surface elements that may occur due to a different polishing process, for example compared to chemically and electrochemically polished metal. Small mounds and holes are observed on the grains, and walls, trenches or steps are observed on the grain boundaries. The development of the different surface elements is orientation-dependent, wherein the orientations of the crystallites are generally arbitrary. The orientations of the grains can be determined by means of electron backscatter diffraction (EBSD), and the roughness and topography can be determined by means of atomic force microscopy (AFM). The result of the analysis can usually be represented by means of EBSD mapping of the analyzed sample region of electrochemically polished metal (for corresponding polishing conditions).

The electropolishing process is a material-removing production method. More precisely, it is an electrochemical removal method using an external power source. In an electrolyte that is specifically tailored to the material, metal is removed anodically, which is to say the metal workpiece forms the anode in an electrochemical cell. The electrochemical removal of parts of the surface shall be briefly described hereafter. The removal generally takes place by way of direct current, however the use of pulsed currents is also possible. The workpiece is switched as the anode. At the industrial level, current densities are applied, which allow removal in the transpassive region of the power density-voltage curve. This causes not only metal to be removed, but also oxygen to develop on the anode, this being the workpiece.

Conventional electrolytes are frequently mixtures of mineral acids and water, and in some cases alcohols. Mixtures of phosphoric acid and sulfuric acid are used for electropolishing stainless steels and steels as well as aluminum alloys. Brass and copper can be treated in mixtures made of phosphoric acid and alcohol. Mixtures made of 55% by weight phosphoric acid and 35% by weight sulfuric acid are also suited for electropolishing aluminum.

Aqueous electrolytes made of 50% by weight phosphoric acid and 30% by weight alcohol, for example 2-propanol, are suited for copper and brass.

According to the invention, a specially selected electrolyte is used so as to subject the surfaces of magnesium alloys, containing zinc and/or aluminum, preferably zinc, as the essential major alloying element, to an electropolishing step. The invention thus relates in particular to a method for producing a microstructured surface, in which the pickling process and/or electropolishing process, preferably the combined pickling and electropolishing process, is carried out using a phosphoric acid-containing electrolyte. For example, an electrolyte that is made of 20% by volume deionized water, 30% by volume phosphoric acid (85% by weight), and 50% by volume ethanol (99% by weight) is suited very well. In the method according to the invention for producing a microstructured surface thus in particular an electrolyte having the following, based on 100% by volume of the electrolyte composition, is used: 15 to 25% by volume deionized water, 25 to 35% by volume phosphoric acid (85±5% by weight), and 45 to 55% by volume ethanol (50±5% by weight), preferably approximately 20% by volume deionized water, approximately 30% by volume phosphoric acid (85±5% by weight) and approximately 50% by volume ethanol (50±5% by weight).

Moreover, surfactants can frequently be admixed to the electrolyte baths. In most cases, the electrolytes are hazardous substances. As a result, knowledgeable handling of the substances is required so as to prevent health and environmental damage.

However, contrary to the actual goal of an electropolishing process, the effect of the present invention is to increase the roughness of the surface of certain magnesium alloys containing zinc and/or aluminum as the major alloying element, so as to improve, for example, the adhesion of polymers, however without reducing the corrosion resistance of the alloy.

Surprisingly, it was found according to the invention that a combination of pickling and electrochemical polishing advantageously achieves the objects of the invention for the aforementioned magnesium alloys. Chemical, electrolytic and/or electrochemical pickling is thus absolutely essential according to the invention, so as to be combined with the electropolishing process or supplement the same.

Pickling, in the technical field, refers to the treatment of solid bodies with a pickle so as to change the surface. This pickling process is used, among other things, to protect the surface against oxidation (in metal). In the prior art, pickling is primarily carried out by partial etching using corrosive chemicals, usually acids or lyes. The process is used, among other things, in electroplating in order to remove applied metal layers or attain an oxide-free surface. The process is often supported by an electrical current. In electroplating, various current-less and current-supported pickling methods are employed. The reason is usually the activation of the base metal for the additional coating. The activation is different for every base metal or alloy. Often times, even minor differences in the alloying constituents may require different pickling methods, in particular with sensitive material such as those used in medical technology.

Surprisingly, the combination according to the invention of pickling and electropolishing advantageously increases the roughness of smooth, and even very smooth surfaces, forming a microstructured surface, in particular for implant and stent applications, whereby the adhesion of polymers is improved and even the corrosion resistance of the alloy as a whole, which is to say without a polymer coating, increases. The improved polymer adhesion manifests itself, for example, in that absorbable polymers such as PLGA, PLLA, PCL and the blends thereof, which are subsequently applied by means of spraying or dip coating, are not impaired in terms of the adhesion thereof to the bulk material of the alloy, even under maximum mechanical stress of the stent. This means that stents having a predetermined design can be dilated up to diameters of 5.2 mm, and the polymer layers do not exhibit any cracks or holes and do not become delaminated. Compared to reference states that are only electropolished, for example, this leads to a degradation time that is extended by at least 4 weeks. Optionally, it is also possible to use polysaccharides. A preferred example for this purpose is polylactide-co-glycolide (PLGA), which is an organic substance based on lactic acid and can be easily decomposed in the human body. As a preferred example, PLGA is used as surgical suture material. PLLA (polylactic acid or polylactide) is also a preferred example and is a thermoplastic aliphatic polyester derived from renewable resources, such as corn starch (in the USA), tapioca roots, chips or starch (mostly in Asia), or sugar cane (in the rest of the world) Tapioka. PLLA is biodegradable under certain conditions, such as in the presence of oxygen, for example. PCL (polycaprolactone) is a biodegradable polyester that has a low melting point of approximately 60° C. and a glass transition temperature of approximately −60° C.

The invention thus has a number of technical advantages over the previously known magnesium alloys and the surfaces thereof, in particular: the degradation time is extended; the degradation process is influenced less by defects; the degradation time thus can be better calculated (variances are reduced); and active agent elution is not impaired by early bulk corrosion. Overall, these unexpected and advantageous properties considerably increase the practical value of medical technology products, such as implants or stents.

The invention will be described in more detail hereafter based on exemplary embodiments.

1. Example

Sleeves made of a magnesium alloy containing 94.75% by weight Mg, 5.0% by weight Zn and 0.25% by weight Ca were extruded between 200° C. and 300° C. by means of forward hollow impact extrusion and at deformation rates between 0.5/s and 3/s. The extrusion was carried out in an impact extrusion device composed of the inner part (punch) and the outer part (die). The sleeve geometry was characterized by an outside diameter between 1.6 mm and 2.4 mm and a wall thickness between 140 µm and 210 µm. The semi-finished product was further processed by means of laser cutting and subsequent processes such as reaming to obtain a stent geometry. Reaming denotes a material-removing production method, which is used for finishing boreholes (especially in metal parts) by way of reaming. This improves both the surface quality and the shape and dimensional accuracy. In order to achieve the surface according to the invention, a combination of etching (pickling) and electropolishing was carried out in a phosphoric acid-containing electrolyte over a total time of approximately 2 minutes. The reamed stents were threaded on titanium wires and immersed in the pickling solution (refer to Example 4). After these steps, the required stent geometry in terms of the strut width (approximately 100 μm) and wall thickness (approximately 120 μm) was obtained. In order to then achieve the desired microstructure effect, a final pickling process was carried out for 10 to 30 seconds in the same electrolyte. This resulted in the microstructuring of the surface, which also includes dissolving of the grains having low corrosion resistance out of the surface (refer to FIG. 1).

Figure 2:
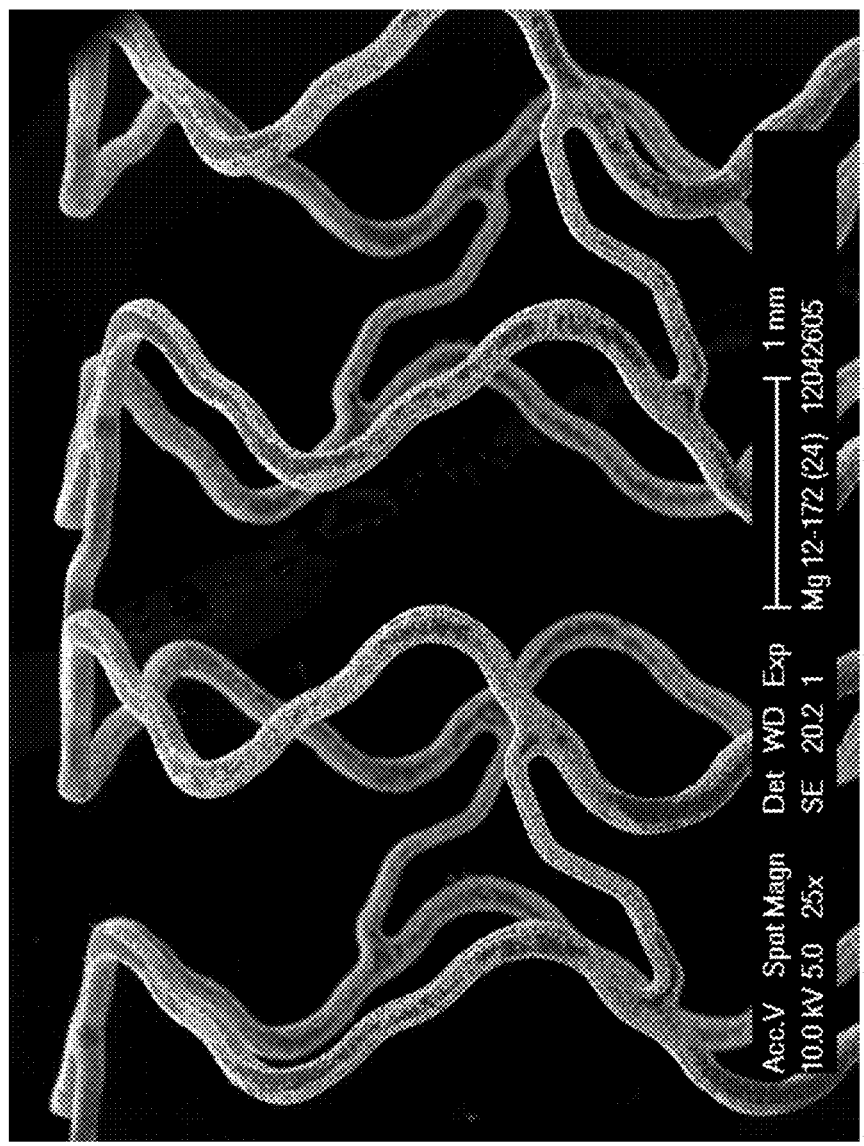
FIG. 2: shows the stent of FIG. 1 after dilatation to 4.00 mm diameter (scanning electron microscopy).
Figure 3:
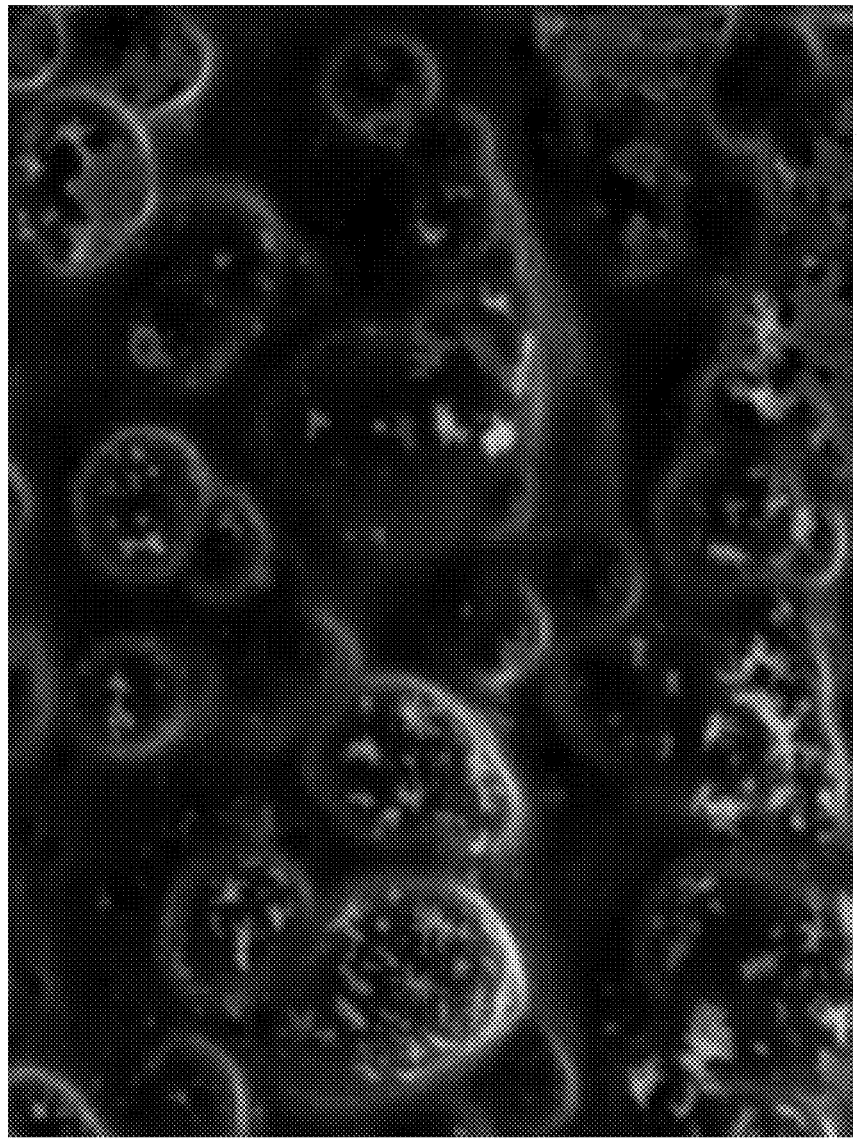
FIG. 3: shows a detail of the microstructured surface with dissolved-out grains (scanning electron microscopy).
Figure 4:
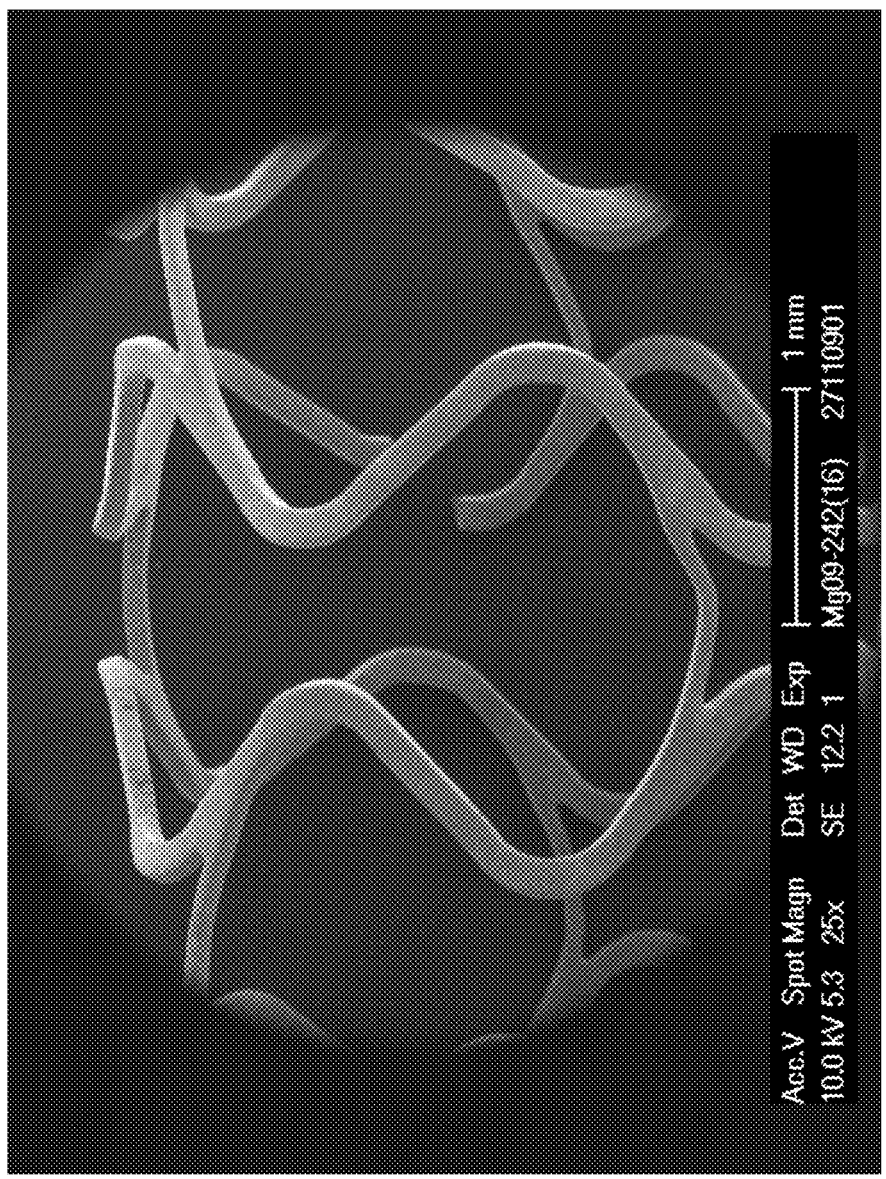
FIG. 4: is a comparison image of a surface without microstructuring (scanning electron microscopy).

With reference to the drawings: FIG. 1 shows the microstructured stent surface according to exemplary embodiment 1 (scanning electron microscopy). This stent surface of the same stent after dilatation from 2.00 mm to 4.00 mm is shown in FIG. 2. FIG. 2 shows the stent of FIG. 1 after dilatation to 4.00 mm diameter (scanning electron microscopy). It was found that the microstructured surface is preserved and no mechanical damage exists. FIG. 3 shows a detail of the microstructured surface with dissolved-out grains (scanning electron microscopy). FIG. 4 is a comparison image of a surface without microstructuring (scanning electron microscopy).

The improved polymer adhesion manifested itself in that absorbable polymers such as PLGA, PLLA, PCL and the blends thereof, which were subsequently applied by means of spraying or dip coating, were not impaired in terms of the adhesion thereof to the bulk, even under maximum mechanical stress of the stent. This means that stents having a predetermined design were able to be dilated up to diameters of 5.2 mm, and the polymer layers did not exhibit any cracks or holes and did not become delaminated. Compared to reference states that were only electropolished, this lead to a degradation time that was extended by at least 4 weeks.

2. Example

Carried out as described in Example 1 for an alloy containing no calcium, which is to say for an alloy composed of 95.0% by weight Mg and 5.0% by weight Zn.

3. Example

Carried out as in Example 1, however with a heat treatment process downstream of the extrusion process at 250° C. over 5 minutes with exposure to air.

Sleeves made of a magnesium alloy containing 94.75% by weight Mg, 5.0% by weight Zn and 0.25% by weight Ca were extruded between 200° C. and 300° C. by means of forward hollow impact extrusion and at deformation rates between 0.5/s and 3/s as in Example 1. The extrusion was carried out in an impact extrusion device composed of the inner part (punch) and the outer part (die). The sleeve geometry was characterized by an outside diameter between 1.6 mm and 2.4 mm and a wall thickness between 140 μm and 210 μm. The semi-finished product was further processed by means of laser cutting and subsequent processes such as reaming to obtain a stent geometry. In order to attain the surface according to the invention, a combination of pickling and electropolishing was carried out in a phosphoric acid-containing electrolyte by way of immersion pickling (refer to Example 4) over a total time of approximately 2 minutes.

The stents on the titanium wire were first chemically pickled (which is to say without current) for approximately 45 seconds. Thereafter, a voltage of 6 V was applied over a period of 1 minute, without the stents leaving the pickling bath. The stents are switched as anodes for this purpose.

A stent having a particular stent design has a total surface of approximately 150 $mm^2$ at a length of approximately 20 mm. At a voltage of 6 V, a current density of approximately 0.05 to 0.15 $A/cm^2$ is present. The flow of current was again interrupted after a time of 45 seconds. The stent then had close to the desired final dimensions and exhibited a relatively smooth surface.

The required stent geometry in terms of the strut width (approximately 100 and wall thickness (approximately 120 μm) was obtained. In order to then achieve the desired microstructure effect, a final pickling process was carried out for 10 to 30 seconds in the same electrolyte. This resulted in the microstructuring of the surface, which also includes dissolving of the grains having low corrosion resistance out of the surface (refer to FIG. 1, for example).

According to the invention, a number of technical advantages of the solution over the previously known magnesium alloys and the surfaces thereof were observed, such as in particular: the degradation time is extended; the degradation process is influenced less by defects; the degradation time thus can be better calculated (variances are reduced); and active agent elution is not impaired by early bulk corrosion. Overall, these unexpected and advantageous properties considerably increase the practical value of medical technology products, such as implants or stents.

4. Example

Description of the electropolishing and pickling processes of magnesium stents.

An electropolishing device is required, composed of: an electrolyte basin and two rinsing basins.

In addition, an electrolyte is required, made of: 20% by volume deionized water, 30% by volume phosphoric acid (85% by weight), and 50% by volume ethanol (99% by weight). The electrolyte can have the following composition, by way of example, expressed in terms of liters: 20 liters deionized water, 30 liters phosphoric acid (85% by weight), and 50 liters ethanol (99% by weight).

The electrolyte is mixed at least 2 days before use in a canister and allowed to rest until it is used.

In addition, cleaning solutions are required, in particular: dimethyl sulfoxide (99.5% by weight) for cleaning basin 1; isopropanol (99.8% by weight) for cleaning basin 2.

Also required are: a polishing rack, consisting of 6 titanium struts with 25 titanium wires in 4 rows, with 5 wires arranged on top of each other in each case; power sources; an eccentric device; and a semi-automatic cleaning system.

To carry out the electropolishing process of magnesium stents, the stents are threaded on the titanium wires, and the wires are fixed on the struts by an additional wire. The electrolyte is mixed by means of a stirrer before every polishing operation. The eccentric device is suspended in the electrolyte basin and the power source, which drives the eccentric disk, is switched on. The polishing time depends on the removal that is desired and ranges between 60 and 300 seconds.

During the first half of the total polishing time, the chemical polishing process takes place and during the second half the electropolishing process takes place, by connecting the polishing rack to a voltage source using two crocodile clips. The voltage source is operated at 6 volts; the current intensity varies with the number of stents on the polishing rack.

After the polishing time has expired, the rack containing the stents is disconnected from the voltage source and removed from the electrolyte solution and placed in a cleaning basin 1, which is filled with dimethyl sulfoxide (99.5%). The cleaning process lasts 2 minutes. The rack is then suspended in a second cleaning basin containing isopropanol for 2 minutes for final cleaning of the polished stents.

The rack containing the stents is then removed from the electropolishing system, the fixed wires are loosened again, and any isopropanol that is still present is removed from the stent. The stent then dries for another 3 to 5 minutes at room temperature on the wire. The dried stent is removed carefully from the wire with a stent remover and undergoes various tests, such as a measurement and visual inspection.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A method for producing a microstructured surface, the method comprising:
    forming a semi-finished product comprising a bioresorbable magnesium alloy with zinc and/or aluminum as a major alloying element, wherein a surface of the semi-finished product has a grain structure having a mean grain size of less than or equal to 10 µm;
    pickling the semi-finished product to dissolve individual grains to produce the microstructured surface of raised grain boundaries with neighboring depressions up to 3 µm deep and up to 10 µm wide; and
    electropolishing the pickled product to smooth surface edges.

2. The method for producing a microstructured surface according to claim 1, characterized in that the magnesium alloy has a heterogeneous and/or no preferred crystallographic orientation.

3. The method for producing a microstructured surface according to claim 1, characterized in that the crystallography of the magnesium alloy does not tend, or tends only insignificantly, toward the formation of secondary phases and/or does not tend, or tends only insignificantly, toward precipitations.

4. The method for producing a microstructured surface according to claim 1, characterized in that the surface comprises grains having differing zinc contents and/or aluminum contents prior to the pickling process.

5. The method for producing a microstructured surface according to claim 1, characterized in that the grain structure has a mean grain size of 1 to 5 µm.

6. The method for producing a microstructured surface according to claim 1, characterized in that the microstructured surface has a microstructure that is made of a grain structure having a mean grain size of 1 to 8 µm.

7. The method for producing a microstructured surface according to claim 1, characterized in that the pickling process and the electropolishing process are carried out using a same phosphoric acid-containing electrolyte.

8. The method for producing a microstructured surface according to claim 7, characterized in that the phosphoric acid containing electrolyte is a composition selected from the group consisting of 15 to 25% by volume or approximately 20% by volume being deionized water; 25 to 35% by volume or approximately 30% by volume being phosphoric acid (85%); and 45 to 55% by volume or approximately 50% by volume being ethanol (50%), based on 100% by volume of the electrolyte composition.

9. The method for producing a microstructured surface according to claim 1, characterized in that the major alloying element is provided in a total quantity selected from the group consisting of 1 to 20% by weight, 3 to 10% by weight, 4 to 7% by weight, and 4.5 to 5.5% by weight.

10. The method for producing a microstructured surface according to claim 1, characterized in that the semi-finished product has zinc and aluminum as a major alloying elements.

11. The method for producing a microstructured surface according to claim 1, characterized in that the semi-finished product is shaped as stent-shaped structure.

12. The method for producing a microstructured surface according to claim 1, characterized in that the magnesium alloy comprises zinc and calcium.

13. The method for producing a microstructured surface according to claim 1, characterized in that the magnesium alloy comprises zinc, and calcium in the following proportions: 94.75% by weight Mg, 5.0% by weight Zn and 0.25% by weight Ca.

14. The method for producing a microstructured surface according to claim 1, characterized in that the magnesium alloy comprises zinc in the following proportions: 95.0% by weight Mg and 5.0% by weight Zn.

15. The method for producing a microstructured surface according to claim 1, the method further comprising pickling the smoothed product after the electropolishing step to dissolve individual grains.

16. The method for producing a microstructured surface according to claim 7, the method further comprising pickling the smoothed product in the same phosphoric acid-containing electrolyte after the electropolishing step to dissolve individual grains.

* * * * *